United States Patent [19]
Langberg

[11] Patent Number: 5,257,635
[45] Date of Patent: Nov. 2, 1993

[54] ELECTRICAL HEATING CATHETER

[75] Inventor: Edwin Langberg, Mount Laurel, N.J.

[73] Assignee: Sensor Electronics, Inc., Mt. Laurel, N.J.

[21] Appl. No.: 736,253

[22] Filed: Jul. 26, 1991

Related U.S. Application Data

[60] Division of Ser. No. 563,562, Aug. 3, 1990, which is a continuation-in-part of Ser. No. 435,361, Nov. 17, 1989, which is a continuation-in-part of Ser. No. 276,294, Nov. 25, 1988, Pat. No. 4,945,912.

[51] Int. Cl.$^5$ .............................. A61N 1/05
[52] U.S. Cl. ................................ 607/122; 606/41
[58] Field of Search .................. 128/784-786, 128/419 P, 804; 606/33, 41, 49

[56] References Cited
U.S. PATENT DOCUMENTS
4,352,360 10/1982 King ................................ 128/786
4,896,671 1/1990 Cunningham et al. .......... 128/786 X

FOREIGN PATENT DOCUMENTS
2822829 11/1979 Fed. Rep. of Germany ...... 128/786
2122092 1/1984 United Kingdom ............. 128/804

*Primary Examiner*—Lee S. Cohen
*Attorney, Agent, or Firm*—Ryan, Kees & Hohenfeldt

[57] ABSTRACT

The invention provides a thermal design of a catheter where the active electrode is partially covered by a heat conducting and electrically insulating heat-sink layer for localizing and controlling an electrical heating of tissue and cooling of the active electrode by convective blood flow. The invention further comprises a current equalizing coating for gradual transition of electrical properties at a boundary of a metallic active electrode and an insulating catheter tube. The current equalizing coating controls current density and the distribution of tissue heating.

13 Claims, 5 Drawing Sheets

ELECTRICAL HEATING CATHETER

This application is a division, of application Ser. No. 07/563,562 filed, Aug. 3, 1990, which is a continuation-in-part of application Ser. No. 07/435,361, filed Nov. 17, 1989 which is a continuation-in-part of application Ser. No. 276,294 filed Nov. 25, 1988, now U.S. Pat. No. 4,945,912.

BACKGROUND

An electrical heating catheter is a tube typically between 1 and 10 millimeters in diameter used for insertion into biological structure and equipped at the distal end with one or more electrodes and at the proximal end with electrical connectors for application of electric power. Electrical heating catheters are useful in many medical applications, e.g., for hyperthermia treatment of cancer or for cardiac ablation of arithmogenic tissue in the endocardium. In such medical applications it is desirable to maintain a fairly uniform generation of heat in a controlled volume of tissue adjoining the catheter.

A radiofrequency (RF) cardiac ablation catheter is presented here as a preferred embodiment. Catheter ablation is a non-surgical method of destroying an arrhythmogenic focus tissue in the endocardium. Typically, an ablation catheter is introduced percutaneously and advanced under fluoroscopic guidance into the left heart ventricle. It is manipulated until the site of the earliest activation is found, indicating the location of problem tissue. RF power is then applied to the distal catheter electrode. The heat in the vicinity of the electrode destroys the cardiac tissue responsible for the arrhythmia.

The temperature boundary between viable and nonviable tissue is approximately 48° Centigrade. Tissue heated to a temperature above 48° C. is non viable and defines the ablation volume. For therapeutic effectiveness the ablation volume must extend a few millimeters into the endocardium and must have a surface cross-section of at least a few millimeters square. The objective is to elevate the basal tissue temperature, generally at 37° C., fairly uniformly to the ablation temperature above 48° C., keeping however the hottest tissue temperature below 100° C. At approximately 100° C. charring and desiccation take place which seriously modifies the electrical conductivity of blood and tissue, and causes an increase in the overall electrical impedance of the electrical heating circuit and a drop in the power delivery to the tissue. Charring is particularly troublesome at the surface of the catheter electrode, since the catheter must be removed and cleaned before the procedure can continue.

In cardiac ablation catheters, the operative electrode is typically metallic and is located on a distal-tip end of the device. This electrode which serves as the heating applicator is referred to as an active electrode. Such an active electrode is the source of electrical or electromagnetic field, which causes heating of neighboring tissue. Even though no significant amount of heat is generated in the electrode itself, adjacently heated endocardial tissue heats the electrode via heat conduction through the tissue.

The field generated by the active electrode also heats the rapid blood flow in the heart chamber, which however very effectively carries away this generated heat so that the flowing blood temperature, except for the boundary layer, stays close to the basal temperature. Some cooling of the catheter tip takes place due to forced convective cooling caused by fast flowing blood in the heart chamber. The active electrode temperature is the result of the balance between such conductive heating and convective cooling.

In one preferred embodiment, the heating and cooling of the active electrode, for the purpose of tip temperature regulation and improved tissue temperature control, is carried out by covering the active electrode with thermally conductive and electrically insulating material. It is therefore appropriate to review the use of dielectric coatings in catheter art and to point out the fundamental difference between the preferred embodiments and the catheter microwave radiator art.

Frequencies for powering heating catheters range from dc to microwaves. It is customary to divide the spectrum of operating frequencies into conductive and radiative regions because of fundamental differences of implementation in these two regions. The dividing frequency between the two regions depends on the characteristic admittance of the tissue surrounding the active electrode: The conductive region is defined by operating frequencies where the conductivity term dominates. Alternatively, in the radiative region the dielectric term dominates. For blood and muscle, the dividing frequency is approximately at 400 MHz. The conductive region corresponds to dc to 400 MHz; the radiative region corresponds to microwave frequencies above 400 MHz.

Implementation of catheter heating applicators for the radiative and the conductive region is quite different. In the radiative region, the heating applicator acts as an antenna causing electromagnetic wave propagation into the tissue. The art of radiative catheter heating applicators, relying on wave propagation, is quite rich, e.g., dipole antennas, helical radiators, and resonators.

An example of a radiative catheter heating applicator, using a resonator, is described in the UK Patent Application GB 2 122 092 A by J. R. James, R. H. Johnson, A. Henderson, and M. H. Ponting. James matches a wave impedance of a resonant radiator, in a mode corresponding to multiples of a quarter wavelength, to a wave impedance of surrounding tissue, by appropriate selection of (1) an electrode coating size, (2) a coating dielectric constant, and (3) a coating magnetic permeability. Neither thermal nor electrical conductivity of the coating is a part of James's design. It should also be noted that the coating in James has both uniform thickness and uniform dielectric properties.

In the conductive region, there is no electromagnetic wave propagation and so techniques relying on wavelength resonance and matching of wave impedance are not applicable. Also in the conductive region, especially in the lower frequencies below 1 MHz, the capacitive impedance of a typical dielectric coating is so high, in comparison with the tissue impedance, that a dielectric coating, in effect, prevents a current flow into the tissue.

Typical state of the art catheter heating applicators for the conductive region, such as the United States Catheter Industries (USCI) catheter shown in FIG. 1, and described in detail later, has an active electrode at the end of the catheter tube and possibly ring electrode or electrodes around the diameter of the tube. Electrodes are connected to the proximal end with a thin, flexible wire.

One undesirable feature associated with such a state-of-the art catheter is a formation of hot spots along the circular junction of the active electrode with the insulating catheter tube due to a sudden transition of electrical properties at the boundary. For example, an article "Catheter ablation without fulguration: Design and performance of a new system", A. J. Ahsan, D. Cunningham, E. Rowland, and A. F. Rickards. *PACE.* Vol. 12, Part II, January: 001–005, 1989 ("Ahsan") shows such formation of hot spots along the circular junction of the active electrode with the insulating catheter tube. To remedy this problem, Ahsan suggests a cylindrical electrode with hemispherical termination at both ends. The problem with Ahsan's solution is that the electrical connection to such an electrode breaks the smoothness of the surface and so generates a hot spot at the junction of the wire with the hemisphere.

The other undesirable feature of the state-of-the art catheter heating applicators is that there is no provision for cooling of the active electrode and as a result, maximum temperature is reached at the electrode and the resultant charring frequently fouls the electrode during a procedure. The temperature profile taken along the axis of the catheter as it extends into the tissue, similar to that shown by the dashed line in Graph (A) in FIG. 2, has been studied by D. E. Haines and D. D. Watson. (PACE Vol. 12, June: 962–976, 1989) and is described in some detail later. It will suffice here to observe that state-of-the-art catheters exhibit the highest temperature at the active electrode and therefore worst charring occurs at the active electrode-tissue boundary.

SUMMARY OF THE INVENTION

The invention provides a thermal design of a catheter where the active electrode is partially covered by a heat conducting and electrically insulating heat-sink layer for localizing and controlling an electrical heating of tissue and cooling of the active electrode by convective blood flow. This design moves peak temperature away from the active electrode surface thus preventing fouling of the active electrode. The cooling provided by the heat-sink layer also increase the depth and volume of an ablation region.

Without the heat-sink layer, as the size of the active electrode increases, the cooling area expands. Simultaneously, the area of current flow increases, thereby increasing the overall heating volume, decreasing the precision of localization of electrical heating; and leading to an undesirable increase in the overall heating power required for ablation.

Additional cooling of the active electrode can be provided by increasing the diameter of an electrical power supply wire, to a cable size so that the cable can carry a significant amount of heat away from the active electrode and dissipates it along the catheter shaft.

The invention further comprises a current equalizing coating for gradual transition of electrical properties at a boundary of a metallic active electrode and an insulating catheter tube. The current equalizing coating controls current density and the distribution of tissue heating. Absence of an abrupt transition in the electrical properties at the catheter tissue boundary, smoothes heat generation and reduces hot spots in tissue.

BRIEF DESCRIPTION OF THE DRAWINGS

FIG. 3 also shows a wire implementation of the heat sink.

DESCRIPTION OF THE PREFERRED EMBODIMENTS

Materials used for the design of the catheter can be conveniently divided into three ranges of electrical resistivity. Metals or metallic materials have resistivity of the order $10^{-6}$ $\Omega$-cm to $10^{-3}$ $\Omega$-cm. The term "conductive" material is used here to describe intermediate materials in the range of resistivity between $10^{-3}$ $\Omega$-cm and $10^5$ $\Omega$-cm. Materials with resistivity larger than $10^5$ $\Omega$-cm are referred to as dielectrics or insulators.

Figure 1:
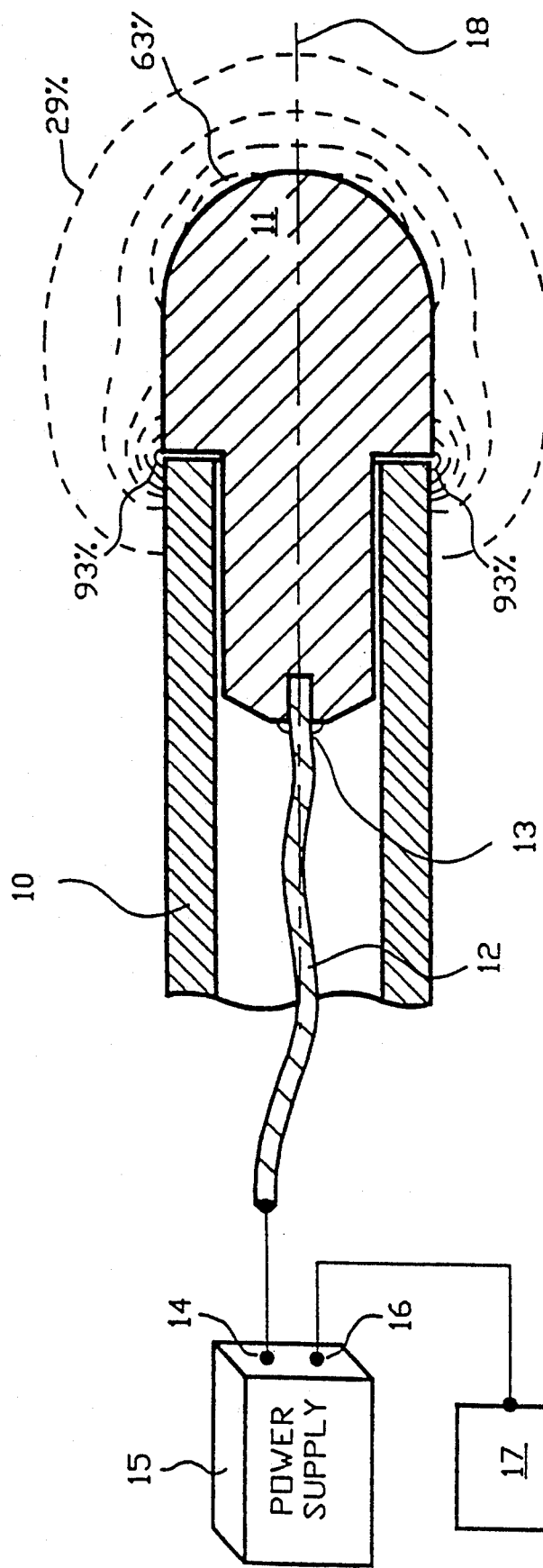
FIG. 1 schematically shows a state-of-the-art catheter system and, in detail, a catheter electrode with the resulting tissue heating power density pattern adjacent to the electrode, indicating formation of a hot spot at the base of the electrode.

FIG. 1 shows a state-of-the-art electrical catheter with an active electrode similar to the standard (USCI) catheter quoted in Ahsan, and referred to in the Background section. The active electrode serves as a heat applicator in distinction to other electrodes which may also be placed on the catheter. A plastic catheter tube 10 connects at a distal end to an active electrode 11, typically made of Platinum. Wire 12 is electrically connected between the active electrode 11 at junction 13 and, at the proximal end of the catheter, to an electrical power source 15, at terminal 14. To maintain flexibility, wire 12 is thin; typical size is 28 gage copper wire with a 0.4 millimeter diameter.

The connection at the proximal end of the catheter to the electrical power source 15 can be between two electrodes on the catheter (bipolar connection, seen later in FIG. 5), or between one active electrode and a large neutral external skin electrode (unipolar connection). A unipolar power supply connection is completed in FIG. 1 by connecting an external skin electrode 17 to a neutral power supply terminal 16. The frequency of operation of the power supply is 450 kHz.

A pattern of dashed lines and associated numbers with a "%" symbol, on the outside of tube 10 and active electrode 11 represent contours of equal heating power density. The percentages associated with pattern lines indicate the relative magnitude of electrical power dissipation in the tissue, with the relative scale adjusted, so that 100% represents maximum dissipation, and 0% represents dissipation at a distant neutral boundary. It should be noted in FIG. 1 that the maximum dissipation ranging from 100% to 93% is in the immediate vicinity of the junction between the metallic active electrode 11 and insulating catheter tube 10. Tissue adjacent to the tip of the active electrode 11 is only in the 63% heating density region. The hot spot at the junction of active electrode 11 and tube 10 acts as an undesirable focus for charring. The temperature of tissue along extension 18 of the catheter axis beyond the tip of active electrode 11 is discussed in connection with FIG. 2.

Figure 2:
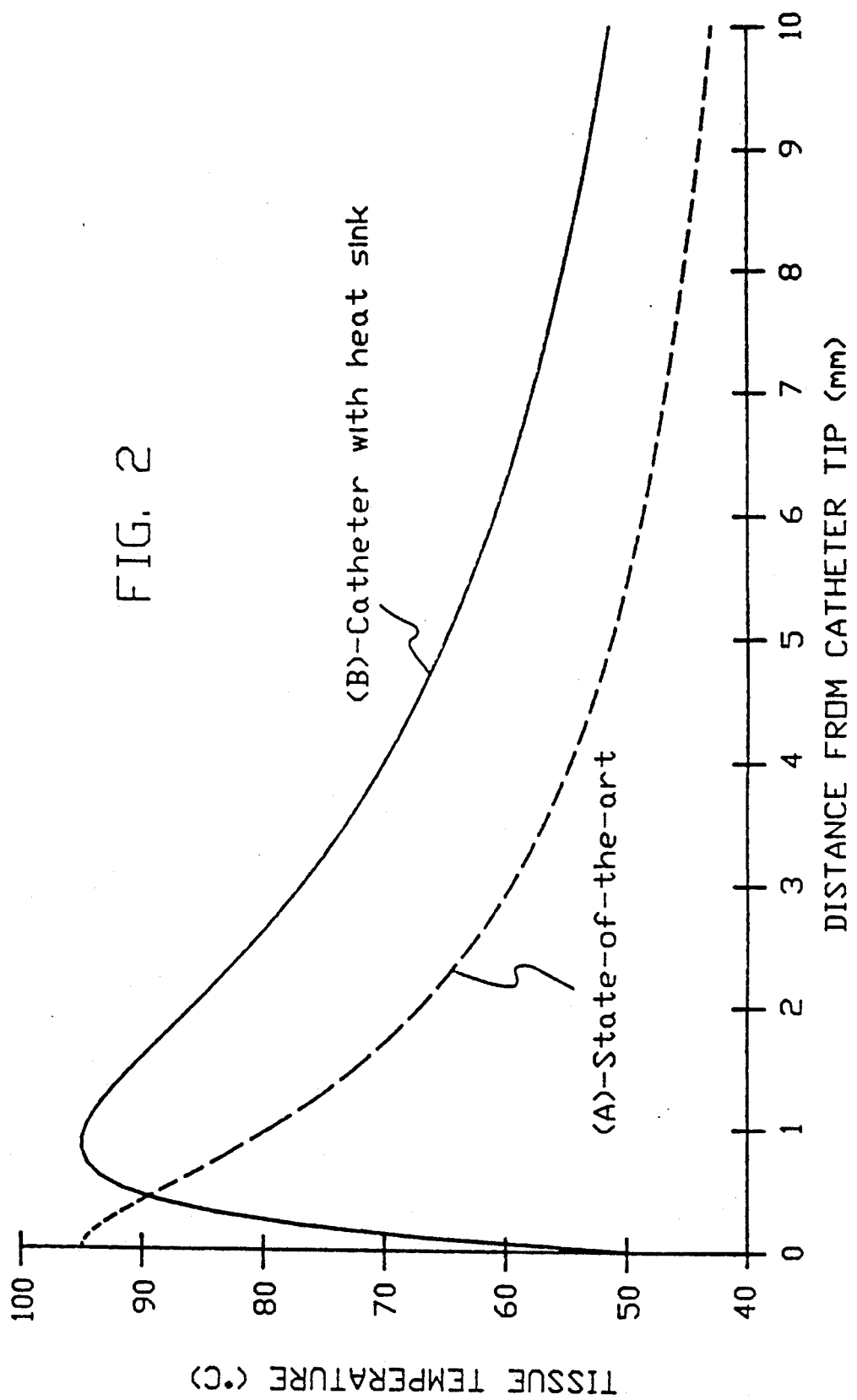
FIG. 2 shows a temperature profile along the extension of the catheter axis into the tissue, produced by (A) the state-of-the-art catheter, and by (B) a catheter with heat sink.

Graph (A) in FIG. 2, shown as a dashed line, is a temperature distribution along extension 18 of the catheter axis produced by the state-of-the-art catheter heating pattern shown in FIG. 1. The temperature is highest directly at the surface of the active electrode (distance=0). In operation, power is typically increased in order to increase the ablation volume until impedance change in noticed due to onset of charring. Since the tissue temperature is highest at the active electrode surface the charring is most likely to take place there. Charring frequently necessitates the removal of the catheter for cleaning.

The objective of the thermal design of a heating catheter is to heat a controlled volume of tissue to a temperature which causes ablation while at the same time assuring that the peak temperature is away from the electrode surface so that charring does not foul the active electrode surface. Graph (B) in FIG. 2 shows such a temperature profile. Graph (B) is described later in conjunction with a heat sink catheter design shown in FIG. 3 and FIG. 4.

Figure 3:
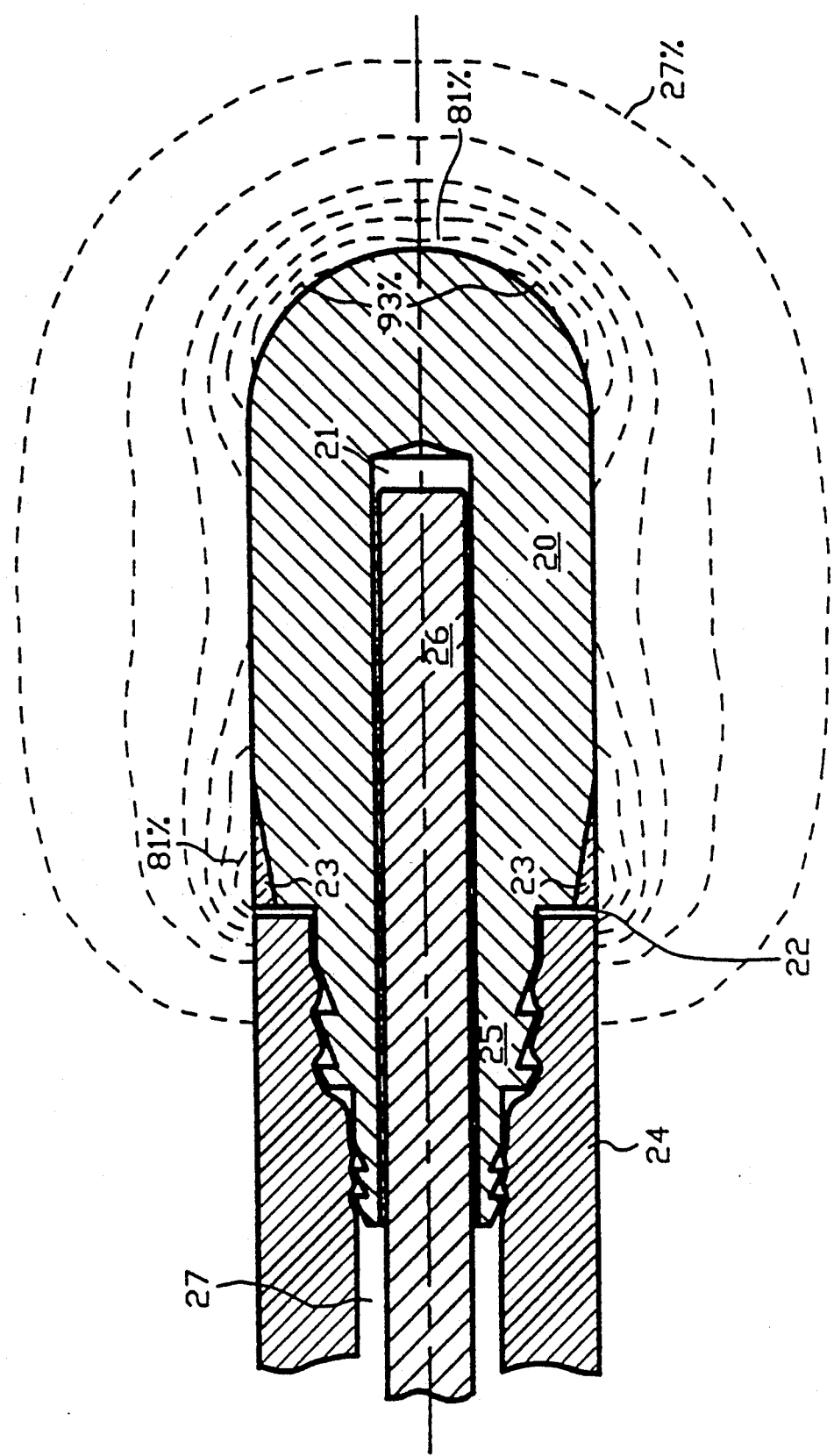
FIG. 3 shows an active electrode with a conductive skirt around the base of the active electrode and shows the resulting equalization of heating power density distribution.

FIG. 3 shows a catheter with improved electrical and thermal design. Axial blind hole 21, in active electrode 20, houses a metallic cable 26. Comparing FIG. 3 with the state-of-the-art catheter in FIG. 1, cable 26 provides an electrical connection to the active electrode 20, as did wire 12 in FIG. 1. Unlike the wire 12, the cross section of cable 26 is much greater, and is typically at least 20% of the cross-section of active electrode 20. Flexibility of cable 26 is maintained by stranded or laminated construction from multiple metallic conductors. Cable 26 provides a much greater heat conduction away from active electrode 20 and into catheter tube 24, thereby reducing a temperature rise of active electrode 20 during operation. Cable 26 also provides a range of possibilities for movable support of active electrode 20. Catheter tube 24 is firmly seated on a undercut protruding proximal end 25 of active electrode 20.

Active electrode 20 is tapered at its base 22 with a tapered angle of 10 degrees. Conductive epoxy fills this tapered region and forms a conductive skirt 23. The contours of equal heating power density, are shown in FIG. 3 for conductive epoxy with resistivity of 150 $\Omega$-cm. The power density percentages, are scaled the same way as in FIG. 1. It can be seen that the uniformity of heating density at the junction of active electrode 20 and tube 24 is much improved when compared with the state-of-the-art catheter in FIG. 1 due to a graduated impedance, presented to the surface current flow, provided by the wedge-shaped cross section of conductive skirt 23.

Such a gradual transition between metallic and insulating surface properties for heating equalization can be accomplished by alternate means to those described above. In one example, conductive skirt 23 is made of uniform thickness but of graduated electrical properties. In another example the transition is implemented by graduated surface capacitance, rather than graduated surface resistance above. A skirt in the form of a tapered deposit of metal oxide on electrode 20 can accomplish such graduated capacitive implementation, e.g., through the formation of a tantalum oxide film, discussed in some detail later.

The impedance graduation need not be accomplished by a surface layer but can if fact extend into the body of the electrode: In yet another implementation, the active electrode is built from axially layered regions of different electrical properties. The direction of current flow can be selectively controlled in individual layers. If radial flow is desired the layer is separated from its neighbors by an insulator and is connected in the center to cable 26. If axial flow is desired the layer is insulted from the cable 26 and electrically joined to its neighbors.

The flow of heat from the electrode 20 is aided by the large cross section of cable 26. The heat flow path in the cable heat sink implementation, shown in FIG. 3, is completed by modification of the catheter tube 24 to increase thermal conductivity from cable 26 to the outside tissue. The heat conductivity of a plastic elastomer material for tube 24 is reduced by embedding heat conductive particles in the material. The region between the cable 26 and the tube 24 is filled with heat conductive paste 27. The technology of improved heat conductivity plastics, and the technology of heat conductive pastes are well established in conjunction with heat sink techniques for solid state devices. In the cable heat sink implementation above, heat dissipated in the tissue, heats active electrode 20. Active electrode 20 in turn, is cooled by heat outflow along cable 26, through the conductive paste 27 and a wall of catheter tube 24 to the blood and tissue surrounding tube 24.

Figure 4:
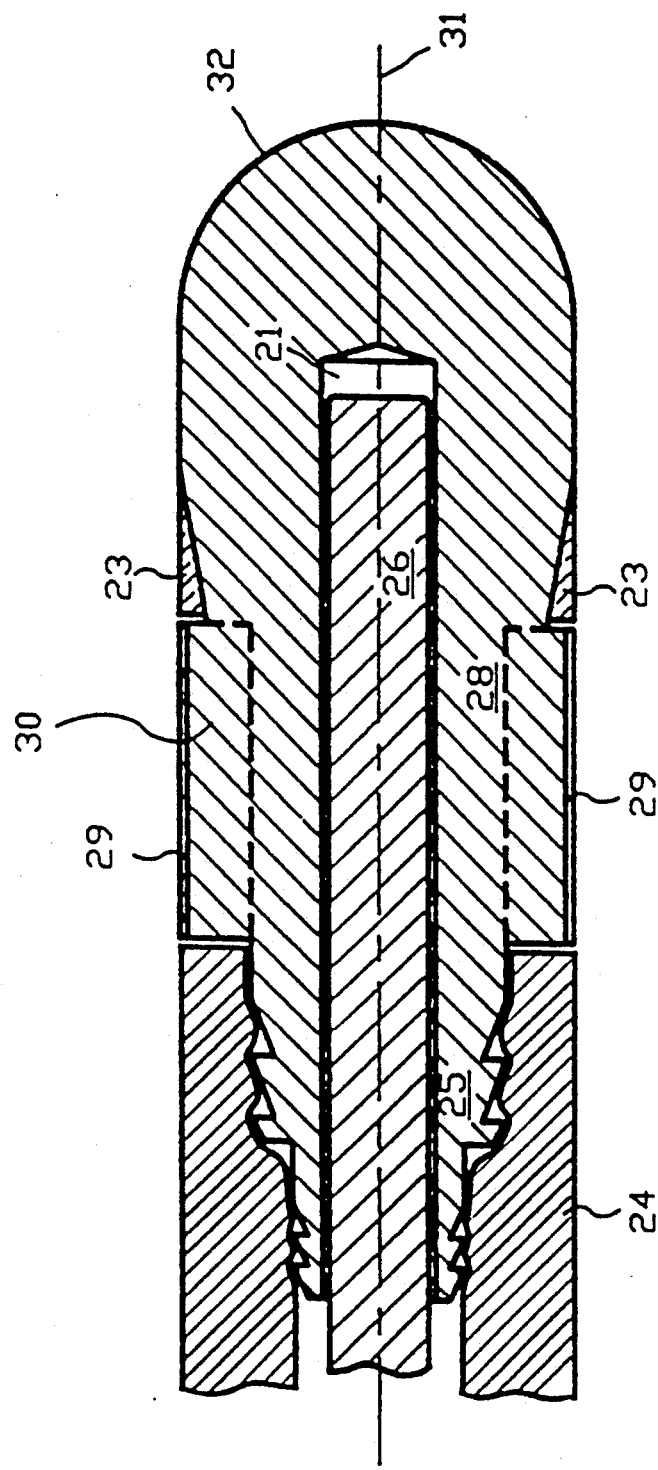
FIG. 4 shows a heat sink in the form of an electrically insulating and thermally conductive film on an active electrode.

FIG. 4 shows an alternative heat sink design. The mounting of cable 26 and tube 24 to active electrode 28 and the function of conductive skirt 23 is substantially the same as described in conjunction with FIG. 3. Active electrode 28 in FIG. 4, preferably made from silver, which is the best heat conductor, has a different shape from active electrode 20 in FIG. 3: Active electrode 28 is longer and is shaped to seat a cylindrical film heat sink 29. The heat sink film 29 is electrically insulating and thermally conductive.

The distal end of active electrode 28 provides a bare metal interface to tissue, generating a heating pattern just as active electrode 20 in FIG. 3. When compared with FIG. 3, the interface between cylindrical film heat sink 29 and the external blood flow provides an added cooling element. The amount of heating and cooling is independently controlled by the ratio of the electrically interacting bare electrode area to the heat sink area.

The overall effectiveness of the heat sink is determined by the thermal conductivity of film 29 and by the heat transfer coefficient. The heat transfer coefficient associated with the thermal boundary layer in forced convection of heat between the catheter surface and the adjacent blood flow, is determined by thermal and hydrodynamic properties of blood. As long as the thermal conductivity of film 29 is significantly smaller than the heat transfer coefficient of the heat convection of the blood flow, the heat sink is close to optimum design. Implementation of heat sink film 29 by a 0.025 mm plastic tube meets this requirement.

The design in FIG. 4 provides very effective forced convective cooling by the flow of blood, while at the same time, allows full control over the size of the area which generates the electrical current flow. It will be noted that the active electrode in FIG. 4 can also comprise the impedance skirt 23 which prevents the formation of a hot spot at the juncture where active electrode 28 and electrically insulating film heat sink 29 meet. The capacitive impedance skirt implementation can be implemented using the same material as heat sink film 29. Cable 26, attached to active electrode 28 provides additional cooling of active electrode 27 by allowing the heat flow into the catheter tube, as previously discussed in conjunction with FIG. 3.

An attractive heat sink/impedance skirt implementation involves a tantalum tube 30 (shown dashed in FIG. 4) which is pressed onto active electrode 28 and so maintains a good thermal and electrical contact with active electrode 28. This tantalum tube is covered by a 0.5 μm thick film of tantalum oxide on its external surface and is graduated to 0 thickness in the skirt area.

It is well known from the technology of tantalum capacitors that a tantalum film only 0.5 μm thick is adequate to provide an electrical insulation with a breakdown voltage in excess of 350 volts. The relative dielectric constant of the tantalum oxide film is 27.6 and so 0.5 μm thick layer 29 produces a capacitance of 8.85 pF to the tissue. At an operating frequency of 300 kHz, this film represents a capacitive reactance of 60 kΩ. When compared with the resistance of the active electrode metal-tissue interface, which is of the order of 100 Ω, the capacitive current through oxide film 29 is insignificant, and film 29 in effect blocks the current flow between the oxide covered tantalum tube 30 and the surrounding tissue and so eliminates electrical heat generation in the tissue surrounding the tantalum oxide heat exchanger.

The same tantalum oxide film 29 has a thermal conductivity of 0.3 watts/(meter C°). For the specified film thickness of 0.5 μm and film area of 12.6 mm², oxide film 29 represents a large thermal conductance of 75.6 watts/C°, which is very adequate for an efficient heat sink.

Graph (B) in FIG. 2 shows the temperature distribution along projection 31 of the axis beyond the distal end of the catheter for an optimized heat sink design in FIG. 4. Comparison of Graph (A) and Graph (B) in FIG. 2 indicates the superior features of the heat sink catheter: The peak temperature is no longer at the catheter surface. The ablation temperature is reached some distance from the catheter surface. Also the ablation region where the tissue temperature is above 48° C. is much larger.

The shape of Graph (B) in FIG. 2 can be adjusted by modification of the ratio of the electrically interacting bare metal active electrode area 32, to the heat sink area 29, and so can be optimized for the requirements of the specific medical procedure.

Figure 5:
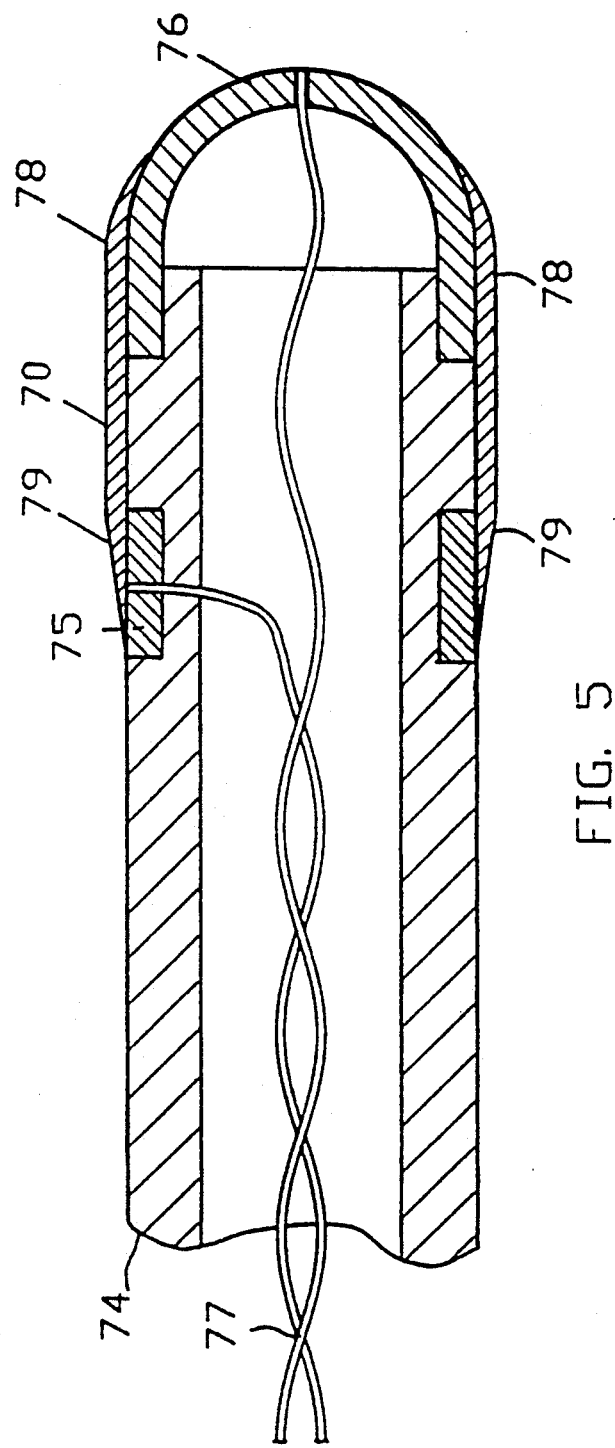
FIG. 5 shows a bipolar catheter with a current equalizing coating.

FIG. 5 shows a proximal ring electrode 75 and a distal tip electrode 76, mounted or plated on a catheter tube 74 and shaped very similarly to the currently used pacing catheters. An electrical connection in maintained by a twisted pair transmission line 77. Unlike currently u&M catheters where the electrodes are made from plain metal, proximal ring electrode 75 and distal tip electrode 76 have their notallic surfaces coated with control coatings 79 and 78 respectively. Optionally, the gap between proximal ring electrode 75 and distal tip electrode 76 can be filled with gap coating 70. (Thickness of coatings is exaggerated in FIG. 5 for the sake of clarity.)

Control coatings 78 and 79 vary in thickness as a function of the axial distance from the inter-electrode gap, being thickest along the edges of the inter-electrode gap and thinning away from the gap. The electrical properties of the uniform thickness coating 70 can be constant or can vary in the axial direction. Without the coatings, the strongest $E_Z$ field in adjacent to the inter-electrode gap. The coatings, by changing the surface impedance, equalize the external electric field and improve radial penetration of the field.

Coatings 78, 79, and 70 can be made from a resistive material or from a dielectric. A resistive coating introduces the highest resistance close to the inter-electrode gap. As a result, the external field adjacent to the inter-electrode gap is reduced, the external field intensity is equalized and the radial penetration is improved. A capacitive coating, made from a dielectric, exhibits a smallest capacitive impedance near the inter-electrode gap and accomplishes field equalization similar to the resistive coating. There is, however, significantly less heat dissipation in the capacitive coating than in the resistive coating.

While certain specific embodiments of improved electrical catheters and systems have been disclosed in the forgoing description it will be understood that various modifications within the scope of the invention may occur to those skilled in the art. Therefore, it is intended that adaptations and modifications should and are intended to be comprehended within the meaning and range of equivalents of the disclosed embodiments.

What is claimed is:

1. An electrical heating catheter comprising:
   an electrical cable housed in an electrically insulating catheter tube;
   the electrical cable adapted to be connected at a proximal end to a source of electrical power;
   an active electrode including a metallic material;
   the electrical cable connected at a distal end to said active electrode;
   a graduated electrical impedance coating on the active electrode for providing a smooth transition of surface current density between said metallic material of the active electrode and a material of the electrically insulating catheter tube.

2. An electrical heating catheter in claim 1 wherein said coating comprises a material with substantially uniform electrical properties and a varying thickness.

3. An electrical heating catheter in claim 2 wherein said material of said coating is conductive epoxy.

4. An electrical heating catheter in claim 2 wherein said material of said coating is a cermet.

5. An electrical heating catheter in claim 2 wherein said material of said coating is a plastic.

6. An electrical heating catheter in claim 2 wherein said material of said coating is a metal oxide.

7. An electrical heating catheter in claim 2 wherein said coating with said varying thickness comprises a conductive skirt surrounding a base of said active electrode, the skirt characterized by a wedge-shaped cross section with a wide face of the wedge against a junction with said electrically insulating catheter tube and a pointy end of the wedge against said metallic material of said active electrode.

8. An electrical heating catheter in claim 1 wherein said graduated electrical impedance coating comprises an electrical material of a substantially uniform thickness and a spatially varying electrical impedance.

9. An electrical heating catheter in claim 1 wherein said graduated electrical impedance coating comprises axially stratified layers, each layer of a substantially constant impedance, and an impedance value graduated from layer to layer.

10. In a catheter for electrical heating, comprising an active electrode formed of metallic material and a catheter transmission line having a proximal end and a distal end, said line being adapted to be connected at its proximal end to a source of electrical power and being connected at its distal end to said active electrode, said electrode in operation being immersed in a lossy medium, said catheter characterized by:
    a graduated impedance coating deposited on a surface of the said active electrode for shaping an electric field in the lossy medium outside of said electrode and coating being heat conducting and electrically insulating, said coating controlling an electrical heating of tissue and cooling of said active electrode by convective blood flow.

11. A catheter for electrical heating in accordance with claim 10, wherein said graduated impedance coating comprises a resistive coating of a varying thickness deposited on the metallic material of said electrode.

12. A catheter for electrical heating in accordance with claim 10, wherein said graduated impedance heat sink coating comprises a dielectric coating of a varying thickness deposited on said metallic material.

13. A catheter for electrical heating in accordance with claim 10, further comprising a graduated electrical impedance coating located in a gap and electrically interacting with said active electrode.

* * * * *

UNITED STATES PATENT AND TRADEMARK OFFICE
CERTIFICATE OF CORRECTION

PATENT NO.  :  5,257,635

DATED       :  November 2, 1993

INVENTOR(S) :  Edwin Langberg

It is certified that error appears in the above-identified patent and that said Letters Patent is hereby corrected as shown below:

Column 8, Line 67:  After "impedance" insert --- heat sink ---

Column 9, Line 10:  Delete "and" first occurrence and substitute --- said ---

Signed and Sealed this

First Day of November, 1994

Attest:

BRUCE LEHMAN

Attesting Officer    Commissioner of Patents and Trademarks